United States Patent
Wojcik, Jr. et al.

(10) Patent No.: US 8,053,478 B1
(45) Date of Patent: Nov. 8, 2011

(54) ANTIMICROBIAL DIARYL IODONIUM COMPOSITIONS AND METHOD

(75) Inventors: Leonard H. Wojcik, Jr., Holladay, UT (US); David D. Cornell, Kingsport, TN (US)

(73) Assignee: Cornell Development Group, LLC, Kingsport, TN (US)

( * ) Notice: Subject to any disclaimer, the term of this patent is extended or adjusted under 35 U.S.C. 154(b) by 540 days.

(21) Appl. No.: 12/138,947

(22) Filed: Jun. 13, 2008

Related U.S. Application Data

(60) Provisional application No. 60/944,551, filed on Jun. 18, 2007.

(51) Int. Cl.
*A01N 29/00* (2006.01)
*A61L 9/00* (2006.01)
*A61L 2/18* (2006.01)

(52) U.S. Cl. .............. 514/743; 422/32; 422/37

(58) Field of Classification Search .......... 514/743
See application file for complete search history.

(56) References Cited

U.S. PATENT DOCUMENTS

| | | |
|---|---|---|
| 3,763,187 A | 10/1973 | Moyle |
| 3,862,333 A | 1/1975 | Chalupa et al. |
| 3,885,036 A | 5/1975 | Moyle |
| 3,944,498 A | 3/1976 | Moyle |
| 6,419,814 B1 | 7/2002 | Pletcher et al. |
| 6,620,305 B2 | 9/2003 | Cornell et al. |
| 6,756,013 B1 | 6/2004 | Cornell et al. |
| 7,052,593 B2 | 5/2006 | Wojcik, Jr. et al. |

OTHER PUBLICATIONS

Ross et al. (Nucleophilic 18 F-Fluorination of Heteroaromatic Iodonium Salts with No-Carrier-Added [18 F] Fluoride, J. Am. Chem. Soc., 2007 (publication date: May 31, 2007), 129 (25), pp. 8018-8025.*

* cited by examiner

*Primary Examiner* — Sreeni Padmanabhan
*Assistant Examiner* — Timothy E Betton
(74) *Attorney, Agent, or Firm* — Whyte Hirschboeck Dudek SC

(57) ABSTRACT

Disclosed are diaryl iodonium compositions with antimicrobial activity and low toxicity to plants and mammals. The present diaryl iodonium compositions include a tri-substituted aryl group and a heteroaryl group which produce substantially no chlorobenzene and/or 1,2-dichlorobenzene when applied to microbes.

5 Claims, No Drawings

ANTIMICROBIAL DIARYL IODONIUM COMPOSITIONS AND METHOD

This application claims priority to and the benefit of U.S. Provisional Patent Application No. 60/944,551, filed Jun. 18, 2007, the entire content of which is incorporated herein by reference.

BACKGROUND

Diaryl iodonium compositions are known antimicrobial agents. Substituted phenyl-thienyl iodonium compositions in particular are effective against bacterial growth, mold, mildew, slime, and viral pathogens. Many substituted phenyl-thienyl iodonium compositions, however, produce undesirable decomposition products such as chlorobenzene and 1,2-dichlorobenzene. Such decomposition products are harmful to mammals including humans.

SUMMARY

The present disclosure sets forth diaryl iodonium compositions with increased antimicrobial effectiveness, low toxicity to plants and mammals, and no, or substantially no, decomposition products which are toxic to mammals including humans.

In an embodiment, an iodonium composition is provided having the following formula:

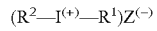

wherein $R^1$ is an aryl group;

$R^2$ is a haloaryl group having a first substituent and a second substituent; and Z, an anion, may be any anion that does not cause decomposition of the iodonium compound. The anion Z can be a halide, a salt of an organic acid, trifluoroacetate, an alkanoate, sulfate, bisulfate, sulfite, phosphate, borate, benzoate, or nitrate.

$R^1$ may be a single aromatic ring, a multiple aromatic ring structure, a polycyclic structure, or a bridged polycyclic structure. In an embodiment, $R^1$ is a heteroaryl group. In a further embodiment, $R^1$ is a thienyl group.

$R^2$ is a haloaryl group with one, two, or more than two halo groups. The halo groups may be the same or different. In an embodiment, $R^2$ is a halophenyl such as chlorophenyl, fluorophenyl, bromophenyl, or iodophenyl. In a further embodiment, $R^2$ is a 4-halophenyl.

One or both of the first substituent and the second substituent may be an alkyl group having 1 to about 18 carbons or an alkoxy group having 1 to about 18 carbons. The first and second substituents may be the same or different. The presence of the halo group in addition to the first substituent and the second substituent on $R^2$ results in a tri-substituted aryl group.

The alkyl group (as well as the alkoxy group) may be a straight aliphatic chain, a branched aliphatic compound, a saturated aliphatic compound, an unsaturated aliphatic compound, a halogen-substituted alkyl, a hydroxy-substituted alkyl, and any combination thereof.

In an embodiment, the composition is substantially free, or free, of decomposition products such as chlorobenzene, 1,2-dichlorobenzene, and combinations thereof.

In an embodiment, a method for controlling microbes is provided. The method includes contacting the microbes with an iodonium composition having the formula:

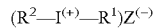

wherein $R^1$ is an aryl group;

$R^2$ is a haloaryl group having a first substituent and a second substituent; and Z is any anion that does not cause decomposition of the iodonium compound, such as a halide, a salt of an organic acid, trifluoroacetate, an alkanoate, sulfate, bisulfate, sulfite, phosphate, borate, benzoate, or nitrate; and producing substantially no decomposition product selected from the group consisting of chlorobenzene, 1,2-dichlorobenzene, and combinations thereof during the contacting.

It is an advantage of the present disclosure to provide diaryl iodonium compositions with increased antimicrobial effectiveness with little or no toxicity to plants or mammals including humans.

It is an advantage of the present disclosure to provide diaryl iodonium compositions that do not produce decomposition products harmful to plants, animals, or humans when placed in contact with microbes.

Additional features and advantages of the present invention are described in, and will be apparent from, the following Detailed Description.

DETAILED DESCRIPTION

The present disclosure is directed to diaryl iodonium compositions which are effective for controlling, killing or otherwise neutralizing such microbes as bacteria, fungi, mold, mildew, fungi, slime and/or viral pathogens. In an embodiment, the iodonium compositions are represented by the following structural formula:

Composition 1

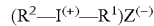

wherein $R^1$ is an aryl group; $R^2$ is a haloaryl group having a first substituent and a second substituent; and an anion Z. Z may be any anion that does not cause decomposition of the iodonium compound. Nonlimiting examples for anion Z include a halide (chloride, hydrochloride, bromide, hydrobromide fluoride, iodide), a salt of an organic acid (oxalates), trifluoroacetate, an alkanoate (such as acetate, diacetate, propionate, dipropionate, butyrate, gluconate, lactate, maleate, valerate, tartrate, bitartrate, metaperdoltartrate, citrate, succinate, besylate, mesylate, tannate, gluceptate, fumarate, oleates, pamoate, octyl methoxycinnamate, octyl salycilate, sub salycilate, pyrrolate, thio malate, hydrochlorothiazide, picolinate, decanonate, undecylenate, glucuronate, guaiacolsulfonate, cypionate, clavvulante, or enanthate), sulfate, bisulfate, polysulfate, thiosulfate, sulfite, phosphate, borate, benzoate, silicate, trisilicate, nitrate, or dinitrate.

As used herein, an "aryl group" is an aromatic substituent which may be a single aromatic ring or multiple aromatic rings which are fused together or linked covalently. In an embodiment, the aryl group represented by $R^1$ is a single ring aromatic compound having from about 4 to about 8 carbons.

Multiple ring aromatic compounds include those compounds having from 2 to about 10 benzene rings such as naphthalene, anthracene, phenathrene, pyrene, 1,2-benzopyrene, coronene and the like.

In an embodiment, $R^1$ may be a polycyclic compound and may include a combination of aromatic compounds and ringed carbon compounds, and/or bridged polycyclic compounds such as azulene, norbornene, and norbornadiene.

In an embodiment, the aryl group may be a heteroaryl group. As used herein, a "heteroaryl group" is one or more aromatic or unsaturated rings in which one or more carbon atoms of the aromatic ring(s) are replaced by a heteroatom(s)

such as oxygen, nitrogen, or sulfur. The heteroaryl group may be a single aromatic ring, multiple aromatic ring(s), or one or more aromatic rings coupled to one or more non-aromatic ring(s). In structures having multiple rings, the rings can be fused together or linked covalently. Nonlimiting examples of suitable heteroaryl groups include pyrrole, pyrazole, imidazole, indole, pyridine, pyridazine, pyrimidine, quinoline, piperidine, pyrrolidine, thiazole, purine, thiophene (i.e., a thienyl group), benzothiophene and furan. In an embodiment, the heteroaryl group is a thienyl group.

Any of the foregoing aryl groups and/or heteroaryl groups may be substituted with groups such as halides, alkyl groups (substituted alkyl, cycloalkyl, substituted cycloalkyl, heterocycloalkyl, substituted heterocycloalkyl), alkoxy groups, vinyl groups, carboxylic acids, esters of carboxylic acids, ethers, alcohols, and epoxides and the like. Suitable alkyl groups have from 1 to about 18 carbons and can be straight chain, cyclic or polycyclic in structure. Suitable alkoxy groups include those having from 1 to about 18 carbon atoms to define a backbone with one or more oxygen atoms interposed therein.

The haloaryl group represented by $R^2$ may include one, two, or more halo substituents. The halo substituents may be the same or different. In an embodiment, the haloaryl group is a halophenyl such as chlorophenyl, fluorophenyl, bromophenyl, and iodophenyl. In a further embodiment, the haloaryl group is a 4-halophenyl group.

The haloaryl group includes a first substituent and a second substituent. Consequently, $R^2$ is at least a tri-substituted (one or more halides, a first substituent, and a second substituent) aryl compound. The first and second substituents may be the same or different. In an embodiment, the first substituent and/or the second substituent may be an alkyl group having 1 to about 18 carbons or an alkoxy group having 1 to about 18 carbons.

The alkyl group (as well as the alkoxy group) may be a straight aliphatic chain, a branched aliphatic, a saturated aliphatic compound, an unsaturated aliphatic compound, and any combination thereof. The alkyl group and/or the alkoxy group may be substituted with halides, hydroxy groups, and any combination thereof.

In an embodiment, an iodonium composition is provided having the following formula:

Composition 2

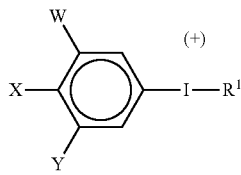

wherein $R^1$ is an aryl group; W is an alkyl group or an alkoxy group; X is a halogen; and Y is an alkyl group or an alkoxy group.

$R^1$ may be any aryl group, heteroaryl group, or polycyclic compound as discussed above. In an embodiment, $R^1$ is a thienyl group. W and Y may be the same or different. W and Y may be any alkyl group or alkoxy group as discussed above.

In an embodiment, Composition 2 may include an anion to form a diaryl iodonium salt. The anion may be any anion that does not cause decomposition of the iodonium compound. Nonlimiting examples for the anion include any anion (i.e., any nonlimiting example for anion Z) discussed above.

In an embodiment, an iodonium composition is provided having the formula:

Composition 3

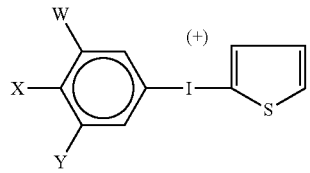

wherein W, X, and Y are selected from the group consisting of a halogen, an alkyl group having 1 to about 18 carbons, an alkoxy group having 1 to about 18 carbons, and combinations thereof. W, X, and Y may be the same or different. Alternatively, any two substituents may be the same with the third substituent being different.

In an embodiment, X is a halo group such as fluoro, chloro, bromo, and iodo. W and Y may be the same or different. In an embodiment, W and Y are each a methyl group and X is a chloro group. In a further embodiment, W and Y are each a methoxy group and X is a chloro group.

In an embodiment, Composition 3 includes an anion. The anion may be any anion as previously discussed herein. The anion may be any anion that does not cause decomposition of the iodonium compound. Nonlimiting examples for the anion may be any anion discussed above.

The present iodonium compositions are potent antimicrobial agents effective in controlling microbes such as bacteria, fungi, mold, mildew, fungi, slime and/or viruses. In addition, the present iodonium compositions advantageously have a low toxicity with respect to mammals and plants. Not wishing to be bound by any particular theory, it is believed provision of 1) a halo group at the 4-position of the phenyl ring in addition to 2) substitutions at the 3- and 5-positions of the phenyl ring synergistically increases antimicrobial efficacy and also reduces mammalian/plant toxicity of the present iodonium compositions.

For example, 4-chlorophenyl-2-thienyliodonium chloride is a known antimicrobial agent with a known antimicrobial efficacy. 4-chlorophenyl-2-thienyliodonium chloride has an oral median lethal dose ($LD_{50}$) of greater than 4000 mg/kg in mice. The present iodonium compositions exhibit antimicrobial activity at least as effective as, or more effective than, 4-chlorophenyl-2-thienyliodonium chloride while simultaneously exhibiting a lack of toxicity to mammals (including humans).

In an embodiment, a method for controlling microbes is provided. The method includes contacting the microbes with an iodonium composition having any of the foregoing formulae. The method further includes producing no, or substantially no, decomposition products such as chlorobenzene, 1,2-dichlorobenzene, and combinations thereof, during contact of the iodonium composition with the microbes.

By way of example and not limitation, examples of the present diaryl iodonium compositions will now be given.

Example 1

4-Iodo-2,6-dimethylalanine was dissolved in concentrated hydrochloric acid at 0° C. Sodium nitrite was added to form a diazo salt. The diazo salt was warmed to room temperature and cuprous chloride added to form 4-iodo-2,6-dimethyl chlorobenzene.

4-Iodo-2,6-dimethyl chlorobenzene was added to a solution of acetic acid, acetic anhydride, with sulfuric acid as an electrolyte and then thiophene and precipitated with potassium bromide in accordance with the procedure of U.S. Pat. No. 7,052,593, the entire content of which is incorporated by reference herein, to produce 3,5-dimethyl 4-chlorophenyl 2-thienyl iodonium bromide. The crude salt was recrystallized from ethanol/water.

Example 2

4-Iodo-2,6-dimethylalanine was dissolved in concentrated hydrochloric acid at 0° C. Sodium nitrite was added to form a diazo salt. The diazo salt was warmed to room temperature and cuprous chloride added to form 4-iodo-2,6-dimenthyl chlorobenzene.

4-Iodo-2,6-dimenthyl chlorobenzene was treated with peracetic acid to form a diacetyl iodo compound. The diacetyl iodo compound was then reacted with thiophene and then with sodium bisulfite to remove excess peroxide. Potassium bromide was then added to precipitate the 3,5-dimethyl 4-chlorophenyl 2-thienyl iodonium bromide salt. The crude salt was recrystallized from ethanol/water.

Nonlimiting examples of specific antimicrobial diaryl iodonium compositions are set forth below.
3,5-dimethyl 4-chlorophenyl 2-thienyl iodonium bromide
3,5-dimethyl 4-chlorophenyl 2-thienyl iodonium chloride
3,5-dimethoxy 4-chlorophenyl, 2-thienyl iodonium bromide
3,5-dimethoxy 4-chlorophenyl 2-thienyl iodonium chloride Example 3

In an experiment challenging the growth of *E. Coli* with measurement of optical density of media, the present iodonium composition, 3,5-dimethyl 4-chlorophenyl 2-thienyl iodonium bromide, suppressed the optical density of the *E. Coli* media at one tenth the concentration needed to accomplish the same optical density reduction utilizing 4-chlorophenyl-2-thienyliodonium bromide. Optical density of the media is a semi-quantitative measure of the presence of growing bacteria. Reduced density indicates the test compounds are retarding bacterial growth. Thus, 3,5-dimethyl 4-chlorophenyl 2-thienyl iodonium bromide, which is non-toxic to mammals, has greater antimicrobial activity than 4-chlorophenyl-2-thienyliodonium bromide.

Example 4

The $MIC_{50}$ (the minimum inhibitory concentration required to inhibit the growth of 50% of organisms) for 3,5-dimethyl 4-chlorophenyl 2-thienyl iodonium bromide applied to several strains of *Staphylococcus aurelius*, including Methicillin-resistant *Staphylococcus aureus* isolates, was found to be one fifth of the $MIC_{50}$ for 4-chlorophenyl 2-thienyl iodonium chloride applied to the same bacteria strains. In tests of toxicity on human epithelial cells both the present iodonium composition, 3,5-dimethyl 4-chlorophenyl 2-thienyl iodonium bromide, and 4-chlorophenyl-2-thienyliodonium bromide at approximate levels of 0.25 millimole concentrations showed a lack of toxicity similar to that of controls. These results show a surprising improvement in antibacterial effectiveness of the 3,5-dimethyl 4-chlorophenyl 2-thienyl iodonium bromide in comparison to the recognized effectiveness of 4-chlorophenyl-2-thienyliodonium chloride. At the same time, present iodonium compound shows lack of human toxicity at use concentrations.

It should be understood that various changes and modifications to the presently preferred embodiments described herein will be apparent to those skilled in the art. Such changes and modifications can be made without departing from the spirit and scope of the present disclosure and without diminishing its intended advantages. It is therefore intended that such changes and modifications be covered by the appended claims.

The invention claimed is:

1. An iodonium composition having the formula

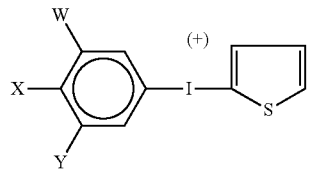

wherein W, X, and Y are selected from the group consisting of a halo group, an alkyl group having 1 to about 18 carbons, an alkoxy group having 1 to about 18 carbons, and combinations thereof.

2. The composition of claim 1 wherein X is a halo group.

3. The composition of claim 1 wherein W and Y are each a methoxy group and X is a chloro group.

4. The composition of claim 1 wherein W and Y are each a methyl group and X is a chloro group.

5. The composition of claim 1 comprising an anion selected from the group consisting of a halide, trifluoroacetate, an alkanoate, sulfate, bisulfate, sulfite, phosphate, borate, benzoate, and nitrate.

* * * * *